United States Patent
Sheehan et al.

(10) Patent No.: US 6,311,163 B1
(45) Date of Patent: Oct. 30, 2001

(54) PRESCRIPTION-CONTROLLED DATA COLLECTION SYSTEM AND METHOD

(76) Inventors: David M. Sheehan, 17515 Valley Verde Rd., Poway, CA (US) 92064; Mark J. Nitzberg, 45-A Fayerweather St., Cambridge, MA (US) 02138; Patrick J. Fitzgerald, 12604 Parish Rd., San Diego, CA (US) 92128

( * ) Notice: Subject to any disclaimer, the term of this patent is extended or adjusted under 35 U.S.C. 154(b) by 0 days.

(21) Appl. No.: 09/426,118

(22) Filed: Oct. 22, 1999

Related U.S. Application Data (60) Provisional application No. 60/105,692, filed on Oct. 26, 1998.

(51) Int. Cl.$^7$ .................................................. G06F 17/60
(52) U.S. Cl. ................................................... 705/2; 705/3
(58) Field of Search .................... 705/1, 2, 3; 707/10, 707/100, 104

(56) References Cited

U.S. PATENT DOCUMENTS

| | | | |
|---|---|---|---|
| 5,258,916 | * 11/1993 | Kroll et al. | 364/401 |
| 5,341,291 | * 8/1994 | Roizen et al. | 364/413.02 |
| 5,822,544 | * 10/1998 | Chaco et al. | 705/2 |
| 5,867,821 | * 2/1999 | Ballantyne et al. | 705/2 |
| 5,897,493 | * 4/1999 | Brown | 600/300 |
| 5,966,692 | * 10/1999 | Langer et al. | 705/3 |
| 5,997,476 | * 12/1999 | Brown | 600/300 |
| 6,055,506 | * 4/2000 | Frasca, Jr. | 705/3 |
| 6,101,478 | * 8/2000 | Brown | 705/2 |

OTHER PUBLICATIONS

"Let's Hear it For the Users! Diagnostic Imaging on the Internet"; *Health Management Technology*, Kohn, D.; Apr. 1997, pp. 14–18.

"A Communication Server for Telemedicine Applications"; *IEEE Transactions on Information Technology in Biomedicine*, Bai , J.B. et al.; vol. 1, No. 3, Sep. 1997, pp. 205–209.

"The Development of Telework in the Health Care Industries"; *Proceedings of the 28$^{th}$ Annual Hawaii International Conference on System Sciences*, Au, G. et al.; 1995, pp. 456–465.

"Multimedia Systems for Telemedicine and Their Communications Requirements"; *IEEE Communications Magazine*, Cabral, Jr., J.E. et al.; Jul. 1996, pp. 20–27.

"An Adaptive Multi–Disciplinary Telemedicine System"; *Proceedings of IMAC*, Chimiak, W.J., et al.; 1995, pp. 244–249.

"Telemedicine Overview and Summary"; *IEEE*, Zach, S.; 1996, pp. 409–412.

* cited by examiner

*Primary Examiner*—Matthew S. Smith
*Assistant Examiner*—Leigh Marie Garbowski
(74) *Attorney, Agent, or Firm*—Lahive & Cockfield LLP (57) ABSTRACT

A prescription-controlled diagnostic data collection system for collecting, storing and receiving medical diagnostic data. A remote medical diagnostic device is configured to collect and transmit diagnostic data. A health service provider prepares a prescription that authorizes the remote diagnostic device to collect and/or transmit diagnostic data. The prescription includes an identifier unique to the device. A central server receives and stores the prescription from the prescribing party and stores status and data information associated with the prescription. A base unit transfer data and authorization information between the remote medical diagnostic device and the server. The remote diagnostic device is operable by a patient independently of the server and the health care provider to collect the diagnostic data, and is operable to transmit the diagnostic data to the server when appropriate authorizations have been received by the base unit from the server.

25 Claims, 4 Drawing Sheets

PRESCRIPTION-CONTROLLED DATA COLLECTION SYSTEM AND METHOD

RELATED APPLICATIONS

This application claims the benefit of U.S. Provisional Application No. 60/105,692, filed on Oct. 26, 1998.

FIELD OF THE INVENTION

The present invention relates generally to data collection systems and, more particularly, relates to a medical diagnosis system in which a doctor communicates a prescription to a remote patient who collects data with a diagnostic device and communicates the data to a server for retrieval by the doctor.

BACKGROUND AND SUMMARY OF THE INVENTION

Broadly speaking, the present invention provides a system and method for collecting, storing and receiving data in a distributed manner based on a remote authorization. In overview, a prescribing party writes a prescription that authorizes a collecting party to collect data and transfer the data to a central server. The status of the prescription and collected data are available to parties having access to the server. The prescription, authorization, status and data information are exchanged via any suitable data communications medium. In one application, a doctor or health care provider at a remote location authorizes a patient to collect and transfer diagnostic data with a medical diagnostic device in a fashion analogous to prescribing drugs.

Significantly, though the device must be authorized or activated in order for data collection to proceed, the data collection process itself is performed by the collecting party or patient independently from, and without involvement of, both the server and the prescribing party. The patient does not, for example, simply respond to prompts or queries provided by the server via the communications medium. This is significant, as the patient can perform the diagnostic procedure at his or her leisure and moreover, can transmit the data to the server at his or her leisure.

In one embodiment of the invention, a system for data collection is provided. The system comprises a data collection device for collecting and/or transmitting data. A prescribing party prepares a prescription that authorize the data collection device to collect and/or transmit data. A server receives and stores the prescription from the prescribing party via a communications medium. The data collection device is operable by a collecting party independently of the server and prescribing party to collect data, and is operable to transmit the data to the server when appropriate authorizations have been received from the server.

In another embodiment of the invention, a prescription-controlled diagnostic data collection system for collecting, storing and receiving medical diagnostic data is provided. The system includes a remote medical diagnostic device that is configured to collect and transmit diagnostic data. A health service provider prepares a prescription that authorizes the remote diagnostic device to collect and/or transmit diagnostic data. The prescription includes an identifier unique to the device. A central server receives and stores the prescription from the prescribing party and stores status and data information associated with the prescription. A base unit transfers data and authorization information between the remote medical diagnostic device and the server. The remote diagnostic device is operable by a patient independently of the server and the health care provider to collect the diagnostic data, and is operable to transmit the diagnostic data to the server when appropriate authorizations have been received by the base unit from the server.

In a further embodiment of the present invention, a method for collecting, storing and receiving data in a distributed manner is provided. The method comprises the following steps:

(a) communicating an operation n authorization for a remote data collection device from a prescribing party to a server;

(b) providing the remote data collection device to a collecting party;

(c) communicating a device identifier from the collecting party to the server;

(d) determining whether the device identified by the device identifier has been authorized for operation by the prescribing party;

(e) if the device is authorized for operation, allowing independent operation of the device by the collecting party to collect data, and if the device has not been authorized for operation, disallowing operation of the device;

(f) communicating the collected data from the device to the server; and (g) on request of the prescribing party, communicating the collected data from the server to the prescribing party.

In a still further embodiment of the present invention, a method for remotely collecting and transmitting diagnostic data is provided. The method comprises the following steps:

(a) communicating a registration of a diagnostic device from a prescribing party to a server;

(b) communicating a prescription from the prescribing party to the server;

(c) providing the diagnostic device to a collecting party;

(d) communicating a device identifier from the collecting party to the server;

(e) determining whether the device has been registered with the server by comparing the registration and the device identifier;

(f) if the device has been registered, communicating the prescription from the server to the device to allow operation of the device, and if the device has not been registered, disallowing operation of the device;

(g) collecting and storing diagnostic data with the device independently of the server and the prescribing party;

(h) determining from the prescription whether the device is authorized to transmit data to the server;

(i) if the device is authorized to transmit data, transmitting the collected data from the device to the server, and if the device is not authorized to transmit data, preventing the transmission of collected data from the device to the server; and (l) on request of the prescribing party, communicating the collected data from the server to the prescribing party.

Objects and advantages of the present invention include any of the foregoing, singly or in combination. Further objects and advantages will be apparent to those of ordinary skill in the art, or will be set forth in the following disclosure.

BRIEF DESCRIPTION OF THE DRAWINGS

The present invention is described with reference to the accompanying drawings. In the drawings, like reference numbers indicate identical or functionally similar elements.

DETAILED DESCRIPTION OF PREFERRED EMBODIMENTS

The present invention provides a system and method for collecting, storing and receiving data in a distributed manner. In one implementation, the data consists of the results of a diagnostic procedure that is collected and stored by a patient. In this implementation, a doctor at a remote location authorizes the patient to collect and transfer the data in a fashion analogous to prescribing drugs.

Figure 1:
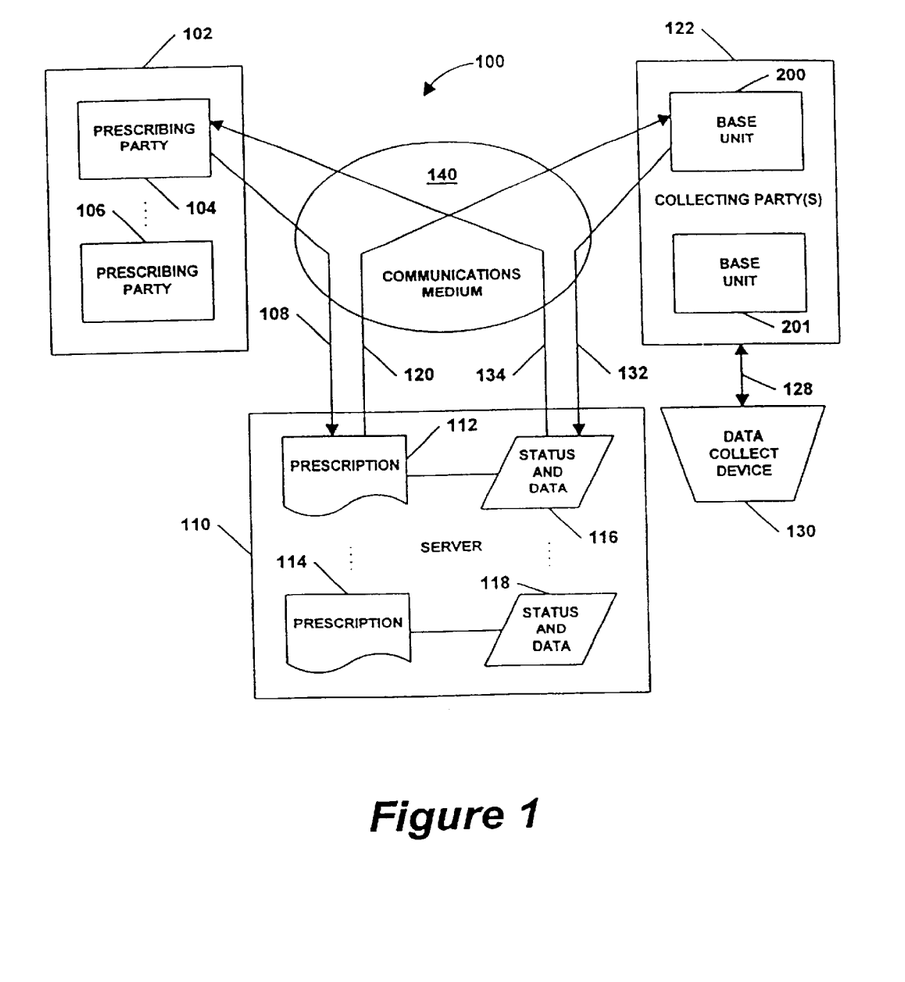
FIG. 1 is a diagram illustrating a prescription controlled data collection system according to the present invention.

A prescription controlled data collection system 100 according to the present invention is illustrated in FIG. 1. In overview, a prescribing party 104 writes a prescription 112 that authorizes a collecting party 122 to collect data and transfer the data to a central server 110. The status of the prescription and data collected (block 116) are available to the prescribing party 104 having access to server 110. The prescription, authorization, status and data informnation (indicated by lines 108, 120, 132 and 134) are exchanged via any suitable data communications medium 140. Medium 140 may comprise any suitable data communications medium including, but not limited to, a wired network, a wireless RF network, a fiber optic network, telephone lines, the Internet or combinations of these mediums.

In a preferred embodiment, system 100 improves the efficiency of medical diagnosis and follow-up by allowing a patient to perform diagnostic and follow-up data collection at a remote location. In this preferred embodiment, prescribing party 104 is a doctor or other health service provider having access to central server 110. As indicated by block 102, a plurality of prescribing parties (doctors) 104 . . . 106 may have access to server 110.

Server 110 may be a computer connected to one or more communications media, such as communication medium 140. Server 110 includes appropriate software that allows transfer of data to and from server 110 from remotely located devices and display terminals. Additionally, server 110 will include appropriate software for handling the protocols for prescribing the use of various remote diagnostic devices and for displaying the status of prescriptions and prescription data. Those of ordinary skill in the art will be familiar with the content and implementation of such software. In one implementation, server 110 may be a "web server" with associated standard communications protocols for communicating over the Internet.

A doctor 104 having access to server 110 prescribes a particular diagnostic procedure to a patient (collecting party) 122 in a remote location by communicating a prescription (indicated by line 108) to a central server 110 over communications medium 140. In one implementation, the prescription authorizes the use of an appropriate diagnostic or data collection device 130 that is in the possession of patient 124.

In a preferred embodiment, the prescription process includes registration of device 130 (whose use by the patient is authorized) with server 110. Registration of device 130 is the process by which server 110 associates device 130 with the doctor or prescribing party 104. In one implementation, a unique device ID number or code identifies device 130 to server 110. This number may be communicated by the prescribing party to the server or, alternatively, assigned by the server to the device. The doctor/device association may be created in server 110 in any suitable fashion. In an implementation where communication medium 140 is the Internet, doctor 140 may effect registration of device 130 by completing a web form that is transmitted via the Internet to server 110. In another implementation where medium 140 takes the form of a telephone network, doctor 104 may effect registration of device 130 by calling a telephone service that prompts the doctor to press appropriate touch-tone buttons on a telephone. In a further implementation, doctor 104 may effect registration by calling or visiting a service whose personnel have access to server 110.

In addition to registration of device 130, the prescription process may also include identification of the doctor 104 to server 110 and identification of the specific data to be collected by the patient. Again, this may be accomplished through use of a web page, a telephone service, or through any other appropriate means. Server 110 may assign each prescription a unique prescription ID number or code. This number will be stored on server 110 (described below), and may also be provided to the prescribing party for future reference.

A prescription may also be designated by a particular type or level of authorization. In one implementation, there are two types of prescriptions: a device use prescription and a data transfer prescription. A device use prescription requires device 130 to receive prescription 112 from server 110 before it can function to collect data for the prescription. A data transfer prescription, conversely, authorizes transfer of data from device 130 to server 10. Hence, once device 130 has been used to collect data (with or without a device use prescription), transfer of the collected data will be blocked unless server 110 has stored a data transfer prescription associated with device 130.

As indicated in FIG. 1, a plurality of prescriptions 112 . . . 114 may be stored on server 110. A variety of information may be stored by server 110 in connection with each prescription. As described above, server 110 will typically assign a prescription ID number or code to each prescription. Where prescription types are used, the prescription type (i.e. device use, data transfer, or other type) will also be noted and stored. The identity (name) of the prescribing party (doctor, health service provider, or other authorized personnel) will typically be stored, as will the name of the patient associated with the prescription. Incident information, such as the health condition prompting the prescription (i.e., "Tim's right eardrum" or "Ellen's heart monitor") may also be stored. Finally, the prescription will include the date of the prescription; and the expiration date (if any) of the prescription. The expiration date of the prescription is the date after which the prescription no longer authorizes the use of device 130 or the transfer of data.

As is also indicated in FIG. 1, server 110 may store status and data information 116 . . . 118 associated with each prescription 112 . . . 114. The status information may be information such as whether device 130 has been activated (yes/no), or whether data has been transferred (yes/no). The data is the information collected by device 130. Examples include, but are not limited to, otoscopic images, heart monitor signals, breathing rhythm data, and so on.

At some time before or after prescribing party 104 communicates prescription 112 to server 110, the patient (collecting party 122) receives an appropriate diagnostic or data collection device 130 and is instructed in its use. Virtually any type of medical diagnostic device is envisioned for use with the present invention, so long as the device is designed to be compatible with base unit 200 (to be described below) that is also provided to the patient. In general, any device that collects diagnostic or follow-up data that can be stored and/or transferred in digital form may be utilized. One suitable device is a digital otoscope as disclosed in U.S. patent application Ser. No. 09/425,499 filed on even date herewith and claiming the benefit of U.S. provisional application No. 60/105,696, which is incorporated herein by reference. Other devices that may be adapted to operate within system 100 include (but are not limited to): rhinoscopes, laryngoscopes, ophthalmoscopes, cameras for dermatology, heart monitors, blood pressure monitors, oxygen saturation monitors, and audio monitors.

Figure 2:
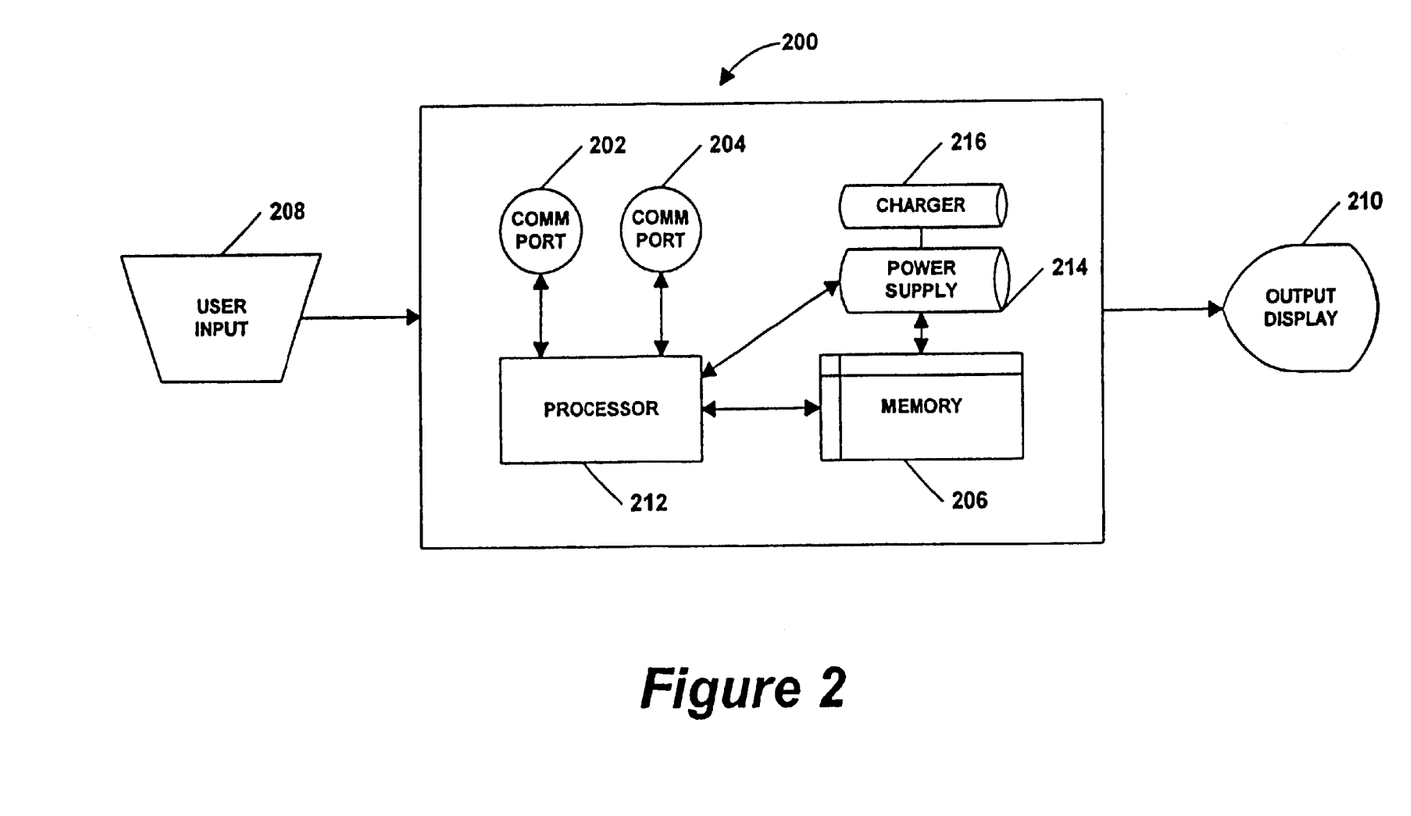
FIG. 2 is a block diagram of a base unit used in conjunction with the prescription controlled data collection system.

As noted above, the patient is instructed in the use of device 130. The amount and type of instruction required will be dependent on the particular device. If device 130 is an otoscope, for example, the patient will be taught how to use the otoscope to capture information from an ear. The patient will also be instructed on how to connect device 130 to base unit 200 and how to effect communications between base unit 200 and server 110.

In addition to a diagnostic device, the patient is provided with a base unit 200 (FIG. 2) for transferring data and authorization information between the device 130 and server 110. Device 130 is suitably designed to be compatible with base unit 200, and communicates with base unit 200 using a standard interface and software protocol. Examples include an RS232 protocol, a Uniyersal Serial Bus protocol, infrared ports, and other suitable protocols as are well known to those of ordinary skill in the art. Any suitable short range data communications medium may be utilized for communication between device 130 and base unit 200, including direct cable, contact connectors (in which case device 130 rests in or is attached to base unit 200), infrared wireless, RF wireless, and so on. Alternatively, device 130 and base unit 200 may be integrated, in which case an external communications medium for communications between unit 200 and device 130 would not be required.

One implementation of base unit 200 is illustrated in block form in FIG. 2. Further details of base unit 200 may be found in U.S. patent application Ser. No. 09/425,499 filed on even date herewith. Base unit 200 includes communications ports 202 nd 204. One of ports 202, 204 communicates with device 130 for data collection, and the other of ports 202, 204 communicates with server 110. In one implementation, communications ports 202 and 204 may be implemented in a modem that interfaces with the Internet or other appropriate communications network.

Base unit 200 also includes a memor 206. Memory 206 provides temporary or permanent storage for data collected by device 130, prescription information provided by server 110, software for implementing the functions of unit 200, user input and preferences, as well as any other information that may be required or of interest. Memory 206 may be implemented as a RAM, ROM or any other suitable storage medium.

Base unit 200 further comprises an input interface or keypad 208. Input 208 may take the form of buttons, keys, dials or any other means that permits a user to enter or provide information and/or data to base unit 200. An output interface 210 is also provided and may comprise a display screen, an LED, an LCD, or other visual display means. Output interface 210 may also provide audio output or announcements to the user.

A processor 212 directs the overall operation of base unit 200. Processor 212 manages data exchange between communication ports 202 and 204, data exchange with memory 206 and input and output interfaces 208 and 210. Processors suitable for carrying out the functions described above are well known to those of ordinary skill in the art. Power supply 214 provides the necessary power to the various components of base unit 200. If power supply 214 is implemented as a battery, a battery charger 216 may also be provided.

Once a prescribing party or doctor has communicated a prescription to server 110 and the collecting party or patient has received an appropriate diagnostic device 130 and base unit 200, server 110 may be required to authorize or activate device 130 to perform its diagnostic function. In one implementation, the patient activates device 130 by downloading prescription 112 from server 110. If configured for device use prescriptions, device 130 will not function until it receives an appropriate prescription from server 110.

In one implementation, in order to activate device 130, the patient connects base unit 200 as is appropriate. This may include, for example, plugging a power line and a telephone line into unit 200. Next, device 130 is appropriately connected to base unit 200, and the user makes an appropriate selection using input interface 208 to initiate communication with server 110. Base unit 200 then communicates the device ID number to server 110 via communications medium 140 (as indicated by line 132 of FIG. 1). Having received the device ID number, server 110 verifies that the device has been registered, retrieves any pending prescriptions 112 . . . 114, and passes the prescriptions onto base unit 200 via communications medium 140 (line 120).

Once base unit 200 has received a prescription and any necessary authorizations from server 110, the collecting party (patient) 124 begins data collection with device 130. The data collected will typically be the results of a diagnostic procedure, such as a heart monitor, otoscope exam, or any other diagnostic procedure. The data collected will typically be stored in a local memory within device 130 until data collection is finished and device 130 is reconnected to base unit 200. Where base unit 200 and device 130 are an integrated unit, the collected data may be transferred directly to memory 206 of base unit 200.

Significantly, though the device must be authorized or activated in order for data collection to proceed, the data collection process itself is performed by the collecting party or patient independently from, and without involvement of, both the server and the prescribing party. The patient does not, for example, simply respond to prompts or queries provided by the server via the communications medium. This is significant, as the patient can perform the diagnostic procedure at his or her leisure and moreover, can transmit the data to the server at his or her leisure.

When the diagnostic procedure data collection is finished, the collected data is transferred from device 130 to server 110. In one implementation, this is accomplished by reconnecting device 130 to base unit 200. The collected data will be communicated from device 130 to base unit 200 via one of the communication ports 202, 204. The user may be required to make an appropriate selection via input interface 208 to accomplish the data transfer. Base unit 200 may store the data in memory 206 and process the data with processor 212. Next, the data is communicated from base unit 200 to server 110 via the other of the communication ports 202, 204. Again, the user may be required to make an appropriate selection via interface 208 to accomplish the transfer. In one implementation, a "send" button may be provided. Moreover, if configured for data transfer prescriptions, base unit 200 verifies that a valid data transfer prescription exists to allow the data to be transferred from device 130.

Once server 110 has received data from a base unit/device under a valid prescription, the data is stored in a status/data file 116 associated with the prescription 112. This data will be available to anyone with authorized access to server 110, typically the prescribing doctor or party. Authorized parties can obtain information about the prescription at any time during the process by communicating with server 110. In one implementation, the available data includes prescription status and prescription data. Prescription status information includes whether device 130 has received the prescription, and whether data has been collected and transferred to server 110. Prescription data includes the data collected and transferred by device 130, and any derivatives of that data resulting from analysis of the data by computer software or otherwise. Authorized personnel may communicate with server using any of the methods described above, i.e., using web forms, touch-tone telephone or telephone service or server personnel, or any other viable method.

Figure 3:
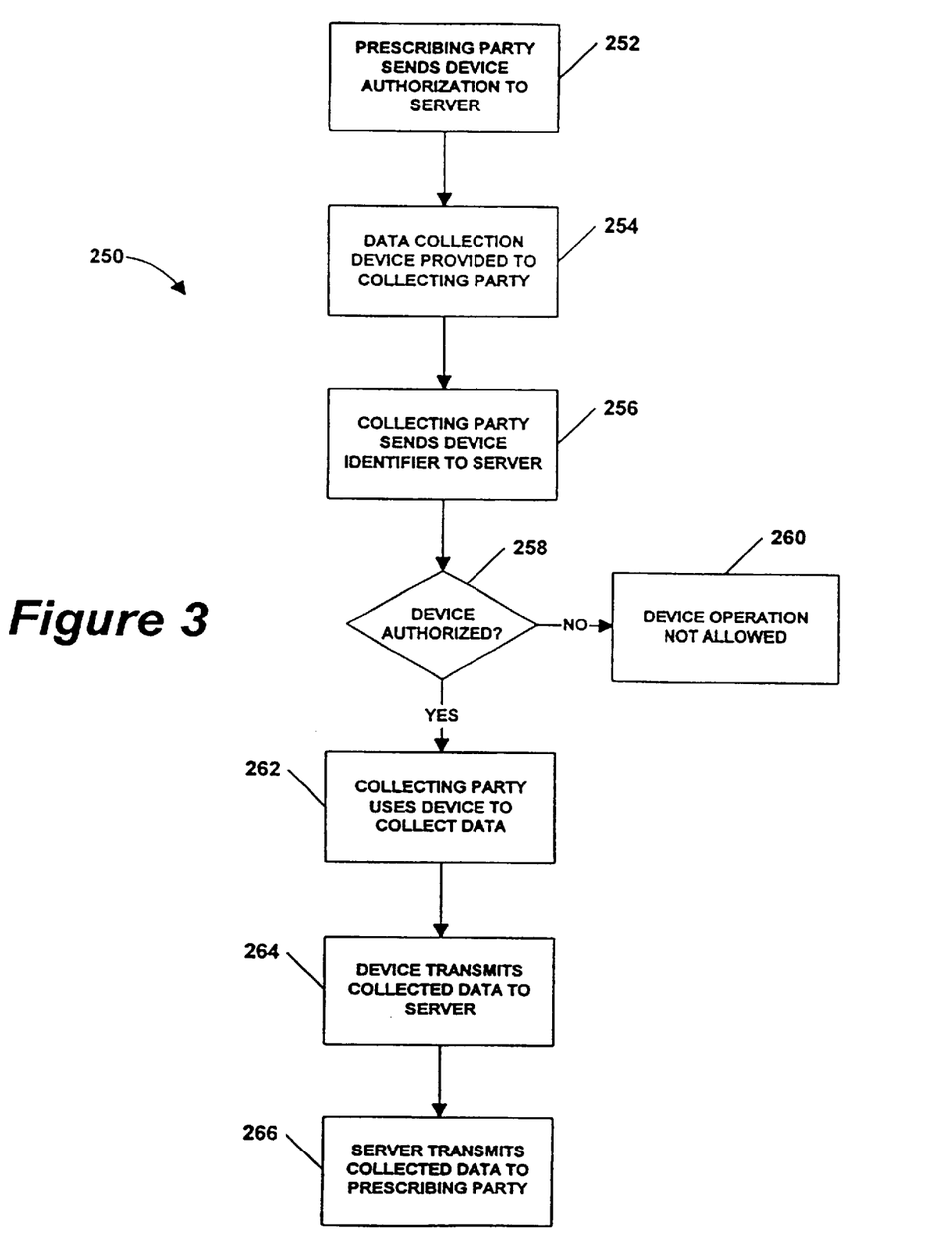
FIG. 3 is a flowchart illustrating a first embodiment of a method for data collection according to the present invention.

FIG. 3 broadly illustrates a first embodiment of a method 250 for collecting, storing and retrieving data in a distributed manner with remote authorization. Method 250 may be implemented using a system 100 as described above. In step 252, a prescribing party communicates an operation authorization for a remote data collection device to a central server. As described above, the device authorization may take the form of a prescription and may include a device ID number or code.

The remote data collection device is provided to a collecting party in step 254. This step may be performed before or after step 252, and the device provided is typically a medical diagnostic device, such as a digital otoscope. In step 256, the collecting party transmits the device identifier to the server, and the server then determines whether the identified device has been authorized for operation by the prescribing party (decision node 258). If the device has not been authorized for operation, in step 260, data collection and transmission is not allowed.

If the device is authorized, the method proceeds to step 262. The device is activated and the collecting party is allowed to independently operate the device to collect data, typically medical diagnostic data. Notably, this operation is performed independently by the device and operator, and does not consist merely of responding to directed prompts or queries of the server or prescribing party. In step 264, the device communicates the collected data to the server, and the server stores the collected data. At the request of the prescribing party, the server transmits the collected data to the prescribing party (step 266).

Figure 4:
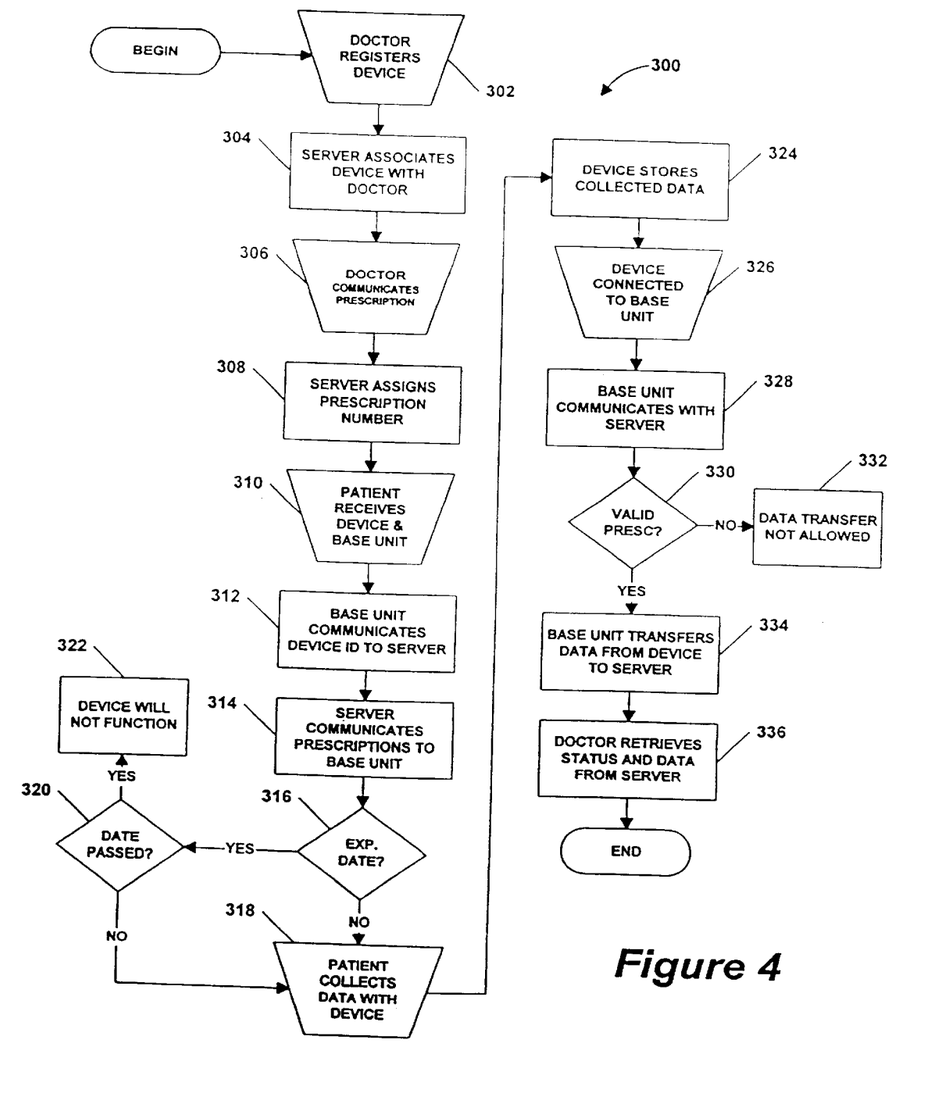
FIG. 4 is a flowchart illustrating a second embodiment of a method for data collection according to the present invention.

A second embodiment of a method 300 for collecting, storing and retrieving data in a distributed manner with remote authorization is illustrated in FIG. 4. Again, method 300 may be implemented in a system such as system 100 of FIG. 1. In step 302, a doctor or other prescribing party registers the diagnostic device with the central server. In step 304, the server associates the registered device with the doctor. As described above, server 110 may assign a unique ID number or code to the registered device, or the prescribing party may communicate a pre-assigned ID number to the server. The doctor then communicates a prescription to the server (step 306). The prescription may include information such as the data to be collected by the patient, a device use and/or data transfer authorization, the names of the patient and doctor, the patient's medical condition, the date and expiration of the prescription, and any other relevant data. Once the prescription has been communicated to the server, the server stores the prescription and assigns a unique ID number or code to the prescription (step 308).

In step 310, the patient receives a diagnostic or data collection device and base unit configured as described above. The patient will also be instructed in their use. Step 310 may occur either before or after the communication of the prescription to the server (steps 302–308). Once a prescription is stored on the server and the patient is in possession of the device and base unit, the base unit communicates the device is activated. In one implementation, the base unit communicates the device ID number to the server, and the server confirms that the device is registered (step 312). If the device is registered, in step 314, the server communicates and pending prescriptions to the base unit.

At decision node 316, the base unit determines whether the prescription has an expiration date. If the prescription does not have an expiration date, the method proceeds directly to step 318 and the patient performs the diagnostic procedure and collects data with the device. If the prescription has an expiration date, the method proceeds to decision node 320 to determine whether the expiration date has passed. The base unit processor will include current clock and calendar information to make this assessment. If there is an expiration date and it has passed, the device will not function to collect data and/or transfer the data to the server. If there is an expiration date but it has not passed, the method proceeds to step 318 to permit commencement of data collection.

The device stores the collected data (step 324), and is reconnected to the base unit in step 326. The base unit will typically receive the collected data from the device and store it in local memory. As described above, if the device and base unit are integrated, this step will not be necessary. In step 328, the base unit communicates with the server to initiate transfer of data from the base unit to the server. Before transfer of data, the base unit and/or the server may determine if a valid prescription or authorization exists to allow the data transfer (step 330). If the base unit is not configured for data transfer prescriptions, this step may not be necessary and data transfer may simply commence (step 334). If, however, the system is configured for data transfer prescriptions and a valid data transfer prescription does not exist, the transfer of data from the base unit to the server is not allowed (step 332). Otherwise, the method proceeds to step 334.

In step 334, the base unit transfers the collected data to the server. The server stores the data and status in a file or memory location associated with the prescription file or memory location. In step 336, the prescribing doctor or other authorized personnel retrieves the status and data from the server. It is important to note that step 336 may be performed at any time throughout the process by personnel having authorized access to the server.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A system for data collection comprising:
   a data collection device for collecting and/or transmitting data
   a prescribing terminal at a remote location to be used by a prescribing party to prepare a prescription, wherein the prescription authorizes the data collection device to collect and/or transmit data; and
   a server that receives and stores the prescription from the prescribing terminal via a communications medium,
   wherein the data collection device is operable by a collecting party independently of the server and prescribing party to collect data, and is operable to transmit the data to the server when appropriate authorizations have been received from the server.

2. A system as claimed in claim 1, wherein the prescribing party is a doctor or health service provider having access to the server, and wherein the data comprises the results of a diagnostic procedure.

3. A system as claimed in claim 1, wherein the communications medium is selected from a group comprising:
   a wired network, a wireless RF network, a fiber optic network, a public telephone network and the Internet.

4. A system as claimed in claim 1, wherein the prescription further comprises a device identifier unique to the data collection device.

5. A system as claimed in claim 4, wherein the server further comprises a unique prescription identifier for each prescription received from the prescribing party.

6. A system as claimed in claim 5, wherein the prescription further comprises at least one authorization selected from a group comprising:
   a device use authorization authorizing the data collection device to gather data; and
   a data transfer authorization authorizing the device to transfer collected data to the server.

7. A system as claimed in claim 5, wherein the prescription further comprises at least one element selected from a group comprising:
   the name of the prescribing party;
   the name of the collecting party associated with the prescription;
   the incident or condition prompting the prescription;
   the date the prescription was given; and
   the expiration date of the prescription.

8. A system as claimed in claim 1, wherein the server further comprises status information and data information associated with the prescription.

9. A system as claimed in claim 8, wherein the status information comprises informnation on whether the data collection device has been activated and/or whether the data collection device has transferred data to the server, and wherein the data information comprises the data gathered by the data collection device and transferred to the server.

10. A system as claimed in claim 1, wherein the data collection device is a medical diagnostic device.

11. A system as claimed in claim 10, wherein the medical diagnostic device is selected from a group comprising:
    an otoscope; a rhinoscope; a laryngoscope; an opthalmoscope; a dermatology camera; a heart monitor; a blood pressure monitor; an oxygen saturation monitor; and an audio monitor.

12. A system as claimed in claim 1, and further comprising a base unit that transfers data and authorization information between the data collection device and the server.

13. A system as claimed in claim 12, wherein the base unit comprises:
    a first communication port for communicating with the data collection device;
    a second communication port for communicating with the server;
    a memory for storing data collected by the data collection device and prescription and authorization information provided by the server;
    user input and output interfaces; and
    a processor for directing the overall operation of the base unit.

14. A system as claimed in claim 13, wherein the first and second communication ports are implemented in a modem.

15. A system as claimed in claim 12, wherein the base unit and data collection device communicate using aprotocol selected from a group comprising:
    an RS232 protocol; a Universal Serial Bus protocol; and an infrared protocol.

16. A system as claimed in claim 12, wherein the base unit and data collection device communicate over a short range data communications medium selected from a group comprising:
    a direct cable connection; contact connectors; an infrared wireless connection; and an RF wireless connection.

17. A prescription-controlled diagnostic data collection system comprising:
    a remote medical diagnostic device for collecting and/or transmitting diagnostic data;
    a prescribing terminal at a remote location to be used by a prescribing party to prepare a prescription, wherein the prescription authorizes the remote diagnostic device to collect and/or transmit diagnostic data and wherein the prescription comprises an identifier unique to the device;
    a server that receives and stores the prescription from the prescribing party via a communications medium, and wherein the server further comprises status and data information associated with the prescription; and
    a base unit that transfers data and authorization information between the remote medical diagnostic device and the server,
    wherein the remote medical diagnostic device is operable by a patient independently of the server and the prescribing party to collect the diagnostic data, and is operable to transmit the diagnostic data to the server when appropriate authorizations have been received by the base unit from the server.

18. A system as claimed in claim 17, wherein the communications medium is the Internet and the server is a web server.

19. A system as claimed in claim 18, wherein the medical diagnostic device is a digital otoscope that communicates with the base unit via contact connectors.

20. A method for collecting, storing and receiving data in a distributed manner comprising the following steps:
    (a) communicating an operation authorization for a remote data collection device from a remotely located prescribing party to a server;
    (b) providing the remote data collection device to a collecting party;
    (c) communicating a device identifier from the remote data collection device to the server;
    (d) determining whether the remote data collection device identified by the device identifier has been authorized for operation by the prescribing party;

(e) if the remote data collection device is authorized for operation, allowing independent operation of the remote data collection device by the collecting party to collect data, and if the remote data collection device has not been authorized for operation, disallowing operation of the remote data collection device;

(f) communicating the collected data from the remote data collection device to the server; and (g) on request of the prescribing party, communicating the collected data from the server to the prescribing party.

21. A method for remotely collecting and transmitting diagnostic data comprising the following steps:

(a) communicating a registration of a diagnostic device from a prescribing party to a server;

(b) communicating a prescription from the prescribing party to the server by remote authorization;

(c) providing the diagnostic device to a collecting party;

(d) communicating a device identifier from the collecting party to the server;

(e) determining whether the diagnostic device has been registered with the server by comparing the registration and the device identifier;

(f) if the diagnostic device has been registered, communicating the prescription from the server to the diagnostic device to allow operation of the diagnostic device, and if the diagnostic device has not been registered, disallowing operation of the diagnostic device;

(g) collecting and storing diagnostic data with the diagnostic device independently of the server and the prescribing party;

(h) determining from the prescription whether the diagnostic device is authorized to transmit data to the server;

(i) if the diagnostic device is authorized to transmit data, transmitting the collected data from the diagnostic device to the server, and if the diagnostic device is not authorized to transmit data, preventing the transmission of collected data from the diagnostic device to the server; and (j) on request of the prescribing party, communicating the collected data from the server to the prescribing party.

22. A method as claimed in claim 21, wherein in steps (a) and (b), the doctor communicates the registration and prescription to the server by a communication means selected from a group comprising:

filling out a web form on the Internet;

calling a telephone service and pressing the appropriate touch-tone buttons; and calling or visiting personnel with access to the server.

23. A method as claimed in claim 21, wherein step (b) further comprises providing at least one type of data selected from a group comprising:

the name of the prescribing party;

the name of the collecting party associated with the prescription;

the incident or condition prompting the prescription;

the date the prescription was given; and the expiration date of the prescription.

24. A method as claimed in claim 23, wherein the expiration date of the prescription is provided by the prescribing party to the server, and comprising an additional step following step (f) of determining whether the expiration date has passed, operation of the device not being allowed if the expiration date has passed.

25. A method as claimed in claim 21, and comprising an additional step wherein the server assigns a unique prescription ID number to the prescription.

* * * * *